United States Patent [19]

Kujira et al.

[11] Patent Number: 4,937,382

[45] Date of Patent: Jun. 26, 1990

[54] PROCESS FOR PREPARING 2-(O-AMINOPHENYL)ETHANOL

[75] Inventors: Katufumi Kujira; Hiroshi Iwane; Makoto Imanari, all of Ibaraki, Japan

[73] Assignee: Research Association for Utilization of Light Oil, Tokyo, Japan

[21] Appl. No.: 288,961

[22] Filed: Dec. 23, 1988

[30] Foreign Application Priority Data

Dec. 24, 1987 [JP] Japan .................................. 62-327872

[51] Int. Cl.$^5$ ............................................. C07C 85/11
[52] U.S. Cl. ..................................... 504/418; 504/420
[58] Field of Search ................................. 564/420, 418

[56] References Cited

U.S. PATENT DOCUMENTS 3,214,473  10/1965  Butts et al. ........................... 564/418

Primary Examiner—Richard L. Raymond
Assistant Examiner—Raymond Covington
Attorney, Agent, or Firm—Oblon, Spivak, McClelland, Maier & Neustadt

[57] ABSTRACT

A process for preparing 2-(o-aminophenyl)ethanol comprising reducing 2-(o-nitrophenyl)ethanol with hydrogen in the presence of a Raney nickel catalyst is described, in which said reducing is carried out in the presence of a small amount of an alkali compound. The Raney nickel catalyst exhibits improved activity to achieve an increased reaction rate.

12 Claims, No Drawings

PROCESS FOR PREPARING 2-(O-AMINOPHENYL)ETHANOL

FIELD OF THE INVENTION

This invention relates to a process for preparing 2-(o-aminophenyl)ethanol useful as a starting material for synthesizing indole, indoline, etc. More particularly, it relates to a process for preparing 2-(o-aminophenyl)ethanol by catalytic reduction of 2-(o-nitrophenyl)ethanol.

BACKGROUND OF THE INVENTION

Reduction of an aromatic nitro group is generally effected by using Raney catalysts, such as Raney nickel, because of their high catalytic activity and inexpensiveness.

The inventors have attempted to obtain 2-(o-aminophenyl)ethanol by reducing 2-(o-nitrophenyl)ethanol in the presence of a Raney nickel catalyst. As a result, it has been turned out that the reaction rate attained is low even when starting with a distillation-purified 2-(o-nitrophenyl)ethanol. That is, it was proved that the Raney nickel catalyst exhibits a lower catalytic activity on this particular reduction reaction than on reduction reactions of other aromatic nitro compounds, e.g., nitrobenzene and nitrotoluene. In order to prepare 2-(o-aminophenyl)ethanol at low cost on an industrial scale, it has been therefore demanded to improve catalytic activity.

SUMMARY OF THE INVENTION

One object of this invention is to provide a process for preparing a 2-(o-aminophenyl)ethanol from 2-(o-nitrophenyl)ethanol with an industrial advantage.

As a result of extensive investigations, it has now been found that this object of the present invention can be accomplished by reducing 2-(o-nitrophenyl)ethanol with hydrogen in the presence of a Raney nickel catalyst, in which a small amount of an alkali compound, e.g., sodium hydroxide, is added to the reaction system.

DETAILED DESCRIPTION OF THE INVENTION

The 2-(o-nitrophenyl)ethanol which can be used as a starting material in the present invention can be synthesized by reacting o-nitrotoluene and formaldehyde in dimethyl sulfoxide or dimethylformamide as a solvent in the presence of a basic catalyst as described in British Patent No. 1,201,209.

The alkali compound which can be used in the present invention includes an alkali metal hydroxide, e.g., lithium hydroxide, sodium hydroxide, and potassium hydroxide. It is added to the reduction system in an amount of from 0.001 to 0.1 mol, preferably from 0.002 to 0.05 mol, particularly preferably from 0.003 to 0.05 mol, per mol of the starting 2-(o-nitrophenyl)ethanol. If the amount is less than 0.001 mol, no substantial effects would be produced. If it is larger than 0.1 mol, reaction selectivity would be reduced considerably.

The catalyst to be used in the reaction may be any of the commercially available developed Raney nickel catalysts and Raney nickel developed in a known manner. The catalyst is usually used in an amount of from about 0.1 to 10% by weight, preferably from about 0.2 to 7% by weight, based on the 2-(o-nitrophenyl)ethanol, but the present invention is by no means limited by the amount of the catalyst.

The reaction can be carried out either in the presence or absence of a solvent, but use of a lower alcohol solvent e.g., methanol and ethanol, is preferred in view of safety against a large quantity of heat generated. The amount of the solvent is not particularly limited and is usually in the range of from about 0.5 to 10 g, preferably from about 0.7 to 7 g, per gram of 2-(o-nitrophenyl)ethanol.

Other reaction conditions are not also limited. In general, the reaction is carried out at a hydrogen pressure of from about 0 to 100 kg/cm$^2$G, preferably from about 1 to 50 kg/cm$^2$G and at a temperature of from room temperature to about 200° C., preferably from about 30° to 150° C.

The present invention is now illustrated in greater detail by way of the following Examples, Comparative Examples, and Reference Examples, but it should be understood that the present invention is not deemed to be limited thereto.

EXAMPLE 1

2-(o-Nitrophenyl)ethanol was synthesized according to the process of British Patent No. 1,201,209 and isolated and purified by distillation (bp: 165°-167° C./6 mmHg).

In a 300 ml-volume autoclave were charged 30 g (0.18 mol) of the resulting 2-(o-nitrophenyl)ethanol, 90 g of methanol, 0.3 g of Raney nickel ("NDT-90", a trade name of Kawaken Fine Chemical Co., Ltd.), and 0.03 g (0.00075 mol) of sodium hydroxide. After displacing the atmosphere with hydrogen several times, the hydrogen pressure was elevated up to 5 kg/cm$^2$G. Then, the temperature was raised while stirring at 1,000 rpm up to 80° C., at which the reaction was commenced. The hydrogen was continuously fed to keep the pressure at 8.5 kg/cm$^2$G. The reaction was completed in 84 minutes, when uptake of hydrogen ceased. The reaction mixture was analyzed by gas chromatography. As a result, the conversion of 2-(o-nitrophenyl)ethanol was 100%, and the yield of 2-(o-aminophenyl)ethanol was 99.1%.

EXAMPLE 2

The same procedure of Example 1 was repeated, except for increasing the amount of sodium hydroxide to 0.09 g (0.0023 mol). After 20 minutes' reaction, no uptake of hydrogen was observed, and the resulting reaction mixture was analyzed by gas chromatography. As a result, the conversion of 2-(o-nitrophenyl)ethanol was 00%, and the yield of 2-(o-aminophenyl)ethanol was 98.9%.

EXAMPLE 3

The same procedure of Example 1 was repeated, except for increasing the amount of sodium hydroxide to 0.12 g (0.003 mol). After 25 minutes' reaction, no uptake of hydrogen was observed, and the reaction was stopped. Gas chromatographic analysis of the reaction mixture revealed that the conversion of the 2-(o-nitrophenyl)ethanol and the yield of 2-(o-aminophenyl)ethanol were 100% and 93.5%, respectively.

EXAMPLE 4

The same procedure of Example 1 was repeated, except for replacing sodium hydroxide with 0.09 g (0.0016 mol) of potassium hydroxide. When uptake of hydrogen ceased in 33 minutes, the reaction was stopped. Gas chromatography of the reaction mixture revealed that the conversion of 2-(o-nitrophenyl)ethanol and the yield of 2-(o-aminophenyl)ethanol were 100% and 98.5%, respectively.

EXAMPLE 5

The same procedure of Example 1 was repeated, except for increasing the amount of sodium hydroxide to 0.06 g (0.0015 mol). When uptake of hydrogen ceased in 43 minutes, the reaction was complete. The reaction mixture was cooled and allowed to stand. The supernatant liquor was recovered by decantation and analyzed by gas chromatography. As a result, the conversion of 2-(o-nitrophenyl)ethanol was 100% and the yield of 2-(o-aminophenyl)ethanol was 99.5%.

EXAMPLE 6

The same procedure of Example 5 was repeated, except for using the catalyst spent in Example 5. The reaction was complete in 74 minutes when uptake of hydrogen ceased. As a result of gas chromatography of the reaction mixture, the conversion of 2-(o-nitrophenyl)ethanol was 100%, and the yield of 2-(o-aminophenyl)ethanol was 99.2%.

COMPARATIVE EXAMPLE 1

In a 300 ml-volume autoclave were charged 30 g (0.18 mol) of 2-(o-nitrophenyl)ethanol isolated and purified by distillation, 90 g of methanol, and 0.3 g of Raney nickel ("NDT-90", a trade name of Kawaken Fine Chemical Co., Ltd.). After displacing the atmosphere with hydrogen several times, the hydrogen pressure was elevated up to 5 kg/cm$^2$G. Then, the temperature was raised up to 80° C. while stirring at 1,000 rpm, at which the reaction started. The hydrogen was continuously fed to keep the pressure at 8.5 kg/cm$^2$G. It was 184 minutes until uptake of hydrogen ceased. The reaction was stopped, and the reaction mixture was cooled and allowed to stand. The supernatant liquor was recovered by decantation and analyzed by gas chromatography. As a result, the conversion of 2-(o-nitrophenyl)ethanol was 100%, and the yield of 2-(o-aminophenyl)ethanol was 98.7%.

COMPARATIVE EXAMPLE 2

The procedure of Comparative Example 1 was repeated, except for using the Raney nickel catalyst spent in Comparative Example 1. The reaction required 300 minutes for completion. As a result of gas chromatography of the reaction mixture, the conversion of 2-(o-nitrophenyl)ethanol was 47.0% and the yield of 2-(o-aminophenyl)ethanol was 42.6%.

REFERENCE EXAMPLE 1

Reduction reaction was carried out in the same manner as in Example 1, except for using 30 g (0.244 mol) of nitrobenzene (reagent grade, produced by Wako Pure Chemical Industries, Ltd.), 90 g of methanol, and 0.3 g of Raney nickel ("NDT-90", a trade name of Kawaken Fine Chemical Co., Ltd.). The reaction was stopped when uptake of hydrogen ceased in 36 minutes. As result of gas chromatography of the reaction mixture, it was found that the conversion of nitrobenzene was 100%.

REFERENCE EXAMPLE 2

The same procedure of Reference Example 1 was repeated, except for further using 0.03 g (0.00075 mol) of sodium hydroxide. The reaction was stopped when uptake of hydrogen ceased in 36 minutes. As a result of gas chromatography of the reaction mixture, it was found that the conversion of nitrobenzene was 100%. It can be seen that the addition of sodium hydroxide produces no appreciable effect on the reaction rate.

While the invention has been described in detail and with reference to specific embodiments thereof, it will be apparent to one skilled in the art that various changes and modifications can be made therein without departing from the spirit and scope thereof.

What is claimed is:

1. A process for preparing 2-(o-aminophenyl)ethanol, comprising:
    reducing 2-(o-nitrophenyl)ethanol with hydrogen in the presence of a Raney nickel catalyst and in the presence of from 0.001 to 0.1 mole per mole of said 2-(o-nitrophenyl)ethanol of an alkali metal hydroxide.

2. A process as claimed in claim 1, wherein said alkali metal hydroxide is lithium hydroxide, sodium hydroxide, or potassium hydroxide.

3. A process as claimed in claim 1, wherein said alkali metal hydroxide compound is present in an amount of from 0.002 to 0.05 mol per mol of the 2-(o-nitrophenyl)ethanol.

4. A process as claimed in claim 3, wherein said alkali metal hydroxide compound is present in an amount of from 0.003 to 0.05 mol per mol of the 2-(o-nitrophenyl)ethanol.

5. The process as claimed in claim 1, wherein the amount of said Raney nickel catalyst in the reduction reaction medium ranges from about 0.1 to 10% by weight based on 2-(o-nitrophenyl)ethanol reactant.

6. The process as claimed in claim 5, wherein the amount of said Raney nickel catalyst ranges from 0.2 to 7% by weight.

7. The process as claimed in claim 1, wherein the reduction reaction is conducted in an alcohol solvent of an amount ranging from 0.5 to 10 g per gram of 2-(o-nitrophenyl)ethanol.

8. The process as claimed in claim 7, wherein said amount of alcohol solvent ranges from 0.7 to 7 g per gram of 2-(o-nitrophenyl)ethanol.

9. The process as claimed in claim 1, wherein the reduction reaction is conducted at a hydrogen pressure ranging from 0 to 100 kg/cm$^2$G.

10. The process as claimed in claim 9, wherein said hydrogen pressure ranges from 1 to 50 kg/cm$^2$G.

11. The process as claimed in claim 1, wherein the reduction reaction is conducted at a temperature ranging from room temperature to about 200° C.

12. The process as claimed in claim 11, wherein said temperature range is from 30° C. to 150° C.

* * * * *